United States Patent [19]

Dedenon et al.

[11] 4,435,188

[45] Mar. 6, 1984

[54] INSTALLATION FOR PREPARING COMBUSTIBLE GASES THROUGH FERMENTATION

[76] Inventors: Jean-Marie Dedenon, 10 Rue du 8 Mai, 77370 Nangis, France; Denis Rassak, 15 Rue Georges Blandon, 78430 Louveciennes, France

[21] Appl. No.: 333,875

[22] PCT Filed: Apr. 17, 1981

[86] PCT No.: PCT/FR81/00053

§ 371 Date: Dec. 17, 1981

§ 102(e) Date: Dec. 17, 1981

[87] PCT Pub. No.: WO81/03030

PCT Pub. Date: Oct. 29, 1981

[30] Foreign Application Priority Data

Apr. 21, 1980 [FR] France .................... 80 08855

[51] Int. Cl.³ .............................................. C02F 3/28
[52] U.S. Cl. ...................................... 48/111; 210/180;
210/195.1; 435/287; 435/299

[58] Field of Search ................... 48/111, 86 R, 197 A;
435/167, 287, 299, 300, 314, 316, 317, 813, 816;
210/173, 180, 195.1; 422/184; 71/10

[56] References Cited

U.S. PATENT DOCUMENTS

| 2,029,702 | 2/1936 | Buswell et al. | 435/819 |
| 2,371,208 | 3/1945 | Alzola | 435/819 |
| 4,022,665 | 5/1977 | Ghosk et al. | 435/819 |
| 4,053,394 | 10/1977 | Fisk | 71/10 |
| 4,100,023 | 7/1978 | McDonald | 71/10 |

FOREIGN PATENT DOCUMENTS 507640 12/1951 Belgium .
898669 10/1943 France .
914808 8/1944 France .
1011722 3/1949 France .

Primary Examiner—Peter F. Kratz
Attorney, Agent, or Firm—Browdy and Neimark

[57] ABSTRACT

The disclosed fermentation installation includes a tank for processing solid materials, a tank for processing diluted substrates, devices for the admission of substrates, product recovery means and interconnecting pipes between the tanks.

4 Claims, 3 Drawing Figures

INSTALLATION FOR PREPARING COMBUSTIBLE GASES THROUGH FERMENTATION

FIELD OF THE INVENTION

The present invention relates to improvements to installations and processes for preparing fuel gases by fermentation. It relates more particularly to anaerobic methane-generating fermentation procedures and to installations for performing these fermentation procedures.

BACKGROUND OF THE INVENTION

It is known how to prepare fuel gases and particularly methane by anaerobic fermentation of masses consisting of agricultural, urban or even industrial organic wastes if they contain sufficient organic matter. In order that the production of the gases may be uninterrupted and the cost competitive, generally the operating methods applied must be continuous operating methods. A continuous process has still other very great advantages, such as, for example, reduction on idle time necessary for cleaning, filling, emptying etc . . . , reduction in the bulk of the equipment as a whole, great facility of operation, possibility of mechanization and automatization of the operations, and increase in the yield due to better choice of operating conditions.

Numerous methane-generating fermentation installations have been described; all the more encouraged by present increased energy needs and the shortage of conventional sources of energy based on petroleum stimulate researchers and producers to use this abundant and cheap raw material constituted by biomass.

Thus:

French Pat. No. 79 05662 describes a process for the preparation of methane from cow manure by anaerobic fermentation, a process that is characterized in that the substrate is introduced into a first preliminary treatment chamber where it is heated to a temperature on the order of 70° C., then maintained at a temperature of about 55°-60° C. while being fed to a second treatment chamber and put in contact with a microorganism culture;

French Pat. No. 77 35966 describes an installation comprising a battery of three tanks arranged one above the other, the fermentation being aerobic in the first and anaerobic in the two others;

French Pat. No. 77 22386 describes a process for methane production by anaerobic fermentation of organic wastes in a fluid-tight fermentation tank completely filled with water;

French Pat. No. 75 09057 describes a digestion installation for organic matter by anaerobic fermentation, the installation comprising a vessel with two compartments communicating through their upper parts;

German Pat. No. 2 535 756 describes a production installation for making methane which consists of a horizontally inclined cylindrical tank provided with an axial stirrer;

U.S. Pat. No. 4,022,665 describes an anaerobic digestion process utilizing organic wastes for methane production; said process comprises two separate steps, a first step for the production of low molecular weight organic acids, and a second step for converting these acid compounds into methane.

Other patents and publications further relate to the preparation of methane by anaerobic fermentation.

Actually, digestion of organic wastes in an anaerobic process has been known for decades. Such a process uses mixed microbial cultures and various substrates. Very many microorganisms are capable of producing methane and they are universally present in nature (marshes, manure, retting of flax, decomposition of organic matter in the soil, degradation of cellulose, etc . . . ). However it has not been possible heretofore to perfect an economically profitable installation, which is sturdy and easy to operate and for use on any farm, which is the main supplier of raw material such as manure, liquid manure, straw, etc . . . . The reasons for this are very simple; and even explain why the solutions specified in the above-cited patents are no longer economically viable. They are principally the following:

Fermentation installations, particularly for continuous fermentation, which are known so far, operate in a dilute aqueous medium. These fermentations approximate the digestion and treatment of sewage, the optimal charge of which is around 8% of organic matter. In continuous fermentation installations, a stirrer or similar device is necessary to break the crust that is formed on the free surface, which serves as a surface for the release of gases produced (holding of the latter is dangerous for the installation). The transfer of the fluids and the stirring action require powerful energy-consuming pumps. Since the overall chemical reaction in this process is very slightly exothermic, the heating and maintenance of the temperature necessary in the mezophilic or thermophilic fermentation zones of the very large mass of water present also consumes much energy. By way of example, it is estimated that the treatment of a mud, having 2% fermentable matter, consumes almost all the methane produced which is used as a fuel to heat and maintain the temperature necessary for operation of the digester. In addition, in the majority of these continuous installations, the residue of the fermentation itself is also too aqueous for direct use as an organic fertilizer.

OBJECTS AND SUMMARY OF THE INVENTION

It is consequently an object of the present invention to provide a process and an installation for the preparation of fuel gases by anaerobic fermentation of organic wastes, which meet the requirements of practice better than the previously known processes and installations used therefor, particularly in that they make possible very considerable energy savings (absence of stirring and development of the fermentation in a more concentrated medium); in that they avoid the formation of "crusts" on the surface, which are especially very dangerous in methane-generating fermentations; in that they make possible mechanized and almost automatic operations; in that they are very easy to handle; in that they are very flexible and make possible treatment both of solid media with variable moisture contents, such as manure, straw, leaves, dry foliage, household waste, etc . . . and liquid media, solutions and aqueous suspensions of various types, such as liquid manures, urine, sewage waters, both continuously, semi-continuously or even in batch; and in that they furnish, on the one hand, a solid fermentation residue of very little moisture content, which is easily transportable and utilizable as fertilizer, and, on the other hand, that they result in a clear liquid without any suspension, which is practically nonpolluting and easily dischargable into sewers and rivers.

The present invention therefore has as its object an installation for the preparation of fuel gases by anaerobic fermentation, characterized in that it comprises in combination: at least a tank for the treatment of solids or of very concentrated substrates (having a dry matter content over 16%), said tank being provided with perforated partitions ensuring drainage substantially over the whole height of the tank holding the solids and allowing the liquids and gases to circulate; at least a tank for the treatment of dilute substrate (the content of which of dry matter is less than 10%) equipped with a heating coil; a device for the introduction of solid substrates; an apparatus for the introduction of liquid substrates; a device for gathering the fermentation residue coming from the solid substrate fermentation tank or tanks; connecting pipes between the solid substrate fermentation tanks and the liquid substrate fermentation tanks, said pipes connecting the fermentation tanks at different levels; and a collecting pipe for the gaseous fermentation products.

According to the invention, the device introducing solid matter is provided with a chopper, an intake pipe for recycling the liquor from the liquid substrate fermentation tank and a drive organ comprising a propelling screw or the like, such as a pump and stirrer which may or may not be terminated by a distributing organ.

According to a particularly advantageous form of this embodiment, the various elements forming the device for introducing solid matter, are arranged so as to form two hydraulic seals successively in the front and rear, between the outer atmosphere and the inner space of the solid substrate fermentation tank.

This device which suitably chops, fluidizes and distributes the solid substrate which feeds the fermentation tank for said substrate, makes it possible not only to have homogeneous composition and particle size for a biomass whch descends easily by gravity but also makes it possible to obtain a homogeneous fermentation residue providing an easy-to-use fertilizer.

According to an advantageous embodiment of the invention, the perforated partition, with which the solid substrate fermentation tank is provided, is in the form of a basket having the shape of said tank.

This basket is placed at some distance from the wall of the tank, particularly to allow the liquid and gas to pass, the solids being retained within it.

According to another embodiment of the invention, the perforated partition, with which the solid substrate fermentation tank is provided, is arranged so as to separate the tank into several zones containing the solid substrate and several zones for the flow of the liquids and gases.

In accordance with the invention, the device for gathering the fermentation residue coming from the solid substrate fermentation tank, is composed of a set of grills equipped with a stripping mechanism for the fermented substrate which is easily maneuverable and with a removal hopper provided with an extraction organ constituting a hydraulic seal for isolating the inner space of the tank.

According to a particularly advantageous embodiment of the invention, the solid substrate fermenter is located above the fermentation tank for the substrate which is liquid and/or in solution to permit the gravity flow of the liquor coming from the upper fermenter to the lower fermenter.

In accordance with the invention, the gas produced in the fermenters is collected directly through the tubes and pipes leaving the fermenters, while a certain amount of this gas passes, before being collected, through the back hydraulic seal of the solid substrate supply device.

This arrangement, although it contaminates the collected methane with air to a slight extent, on the other hand, makes it possible to the apparatus in a completely anaerobic atmosphere.

The invention also has as its object a process for the preparation of fuel gases by anaerobic fermentation, characterized in that a solid substrate is charged, isolated from the atmosphere, into a solid substrate fermentation tank, which may already be partly filled with other substrate previously introduced in the same manner. In the course of fermentation, the said solid substrate may be chopped by a chopper in the feed device, the introduction of the substrate being, if necessary, facilitated by the admission into the feed device of the fermentation liquor coming from a liquid substrate fermentation tank. The lower layers of the solid substrate are proportionately removed by a device for gathering the fermentation residue, the frequency and the flow rates of the supply and the removal being coordinated so that the substrate stays in the fermentation tank between about one and sixty days. The liquid juice flows into the liquid substrate fermentation tank situated generally below the solid substrate fermentation tank, while the gas produced is collected through pipes provided for this purpose and, the liquid and/or dissolved substrate is charged, shielded from atmospheric air, into a liquid substrate fermentation tank, said tank being provided with a coil for heating the liquids, with means for recycling the liquor to the solid substrate fermentation tank and with pipes for collecting the gas produced.

Thus, each time a fresh layer of solid substrate is introduced, it is possible to remove a layer of the digested substrate, the rate and stay time being a function of the quality of the starting substrate and of the quality of the digested substrate, i.e., of the fertilizer desired.

The recycling liquor coming from the liquid digester fulfills several functions: by flowing from and through the solid substrate contained in the solid substrate tank, which constitutes with its system of perforated partitions a sort of percolator, it is freed from solid particles in suspension and thus there is clarification of the liquor which can be discharged without inconvenience; on the other hand, being heated by the presence of a heating coil in the liquid substrate tank, it permits, if desired, the heating and maintenance of the biomass in one or more solid substrate tanks at the desired temperature.

Recycling of this liquor also makes it possible to:
control the acidity of the medium of the solid substrate fermenter;
adjust the moisture level of the biomass; and
have a sort of permanent "tank-bottom ferment" facilitating rapid starting of fermentation of freshly introduced material.

Besides the foregoing features, the invention comprises yet other features, which will become apparent from the description which follows.

The present invention is directed more particularly to processes and installations for fuel gas production in accordance with the foregoing arrangements and the means suitable for using these processes. The embodiment of these installations, and the processes as a whole and production lines in which the processes and installations according to the present invention are included will likewise become clear from the description below.

BRIEF DESCRIPTION OF THE DRAWINGS

The invention will be better understood by the description which follows, which refers to the accompanying drawings in which.

Figure 1:
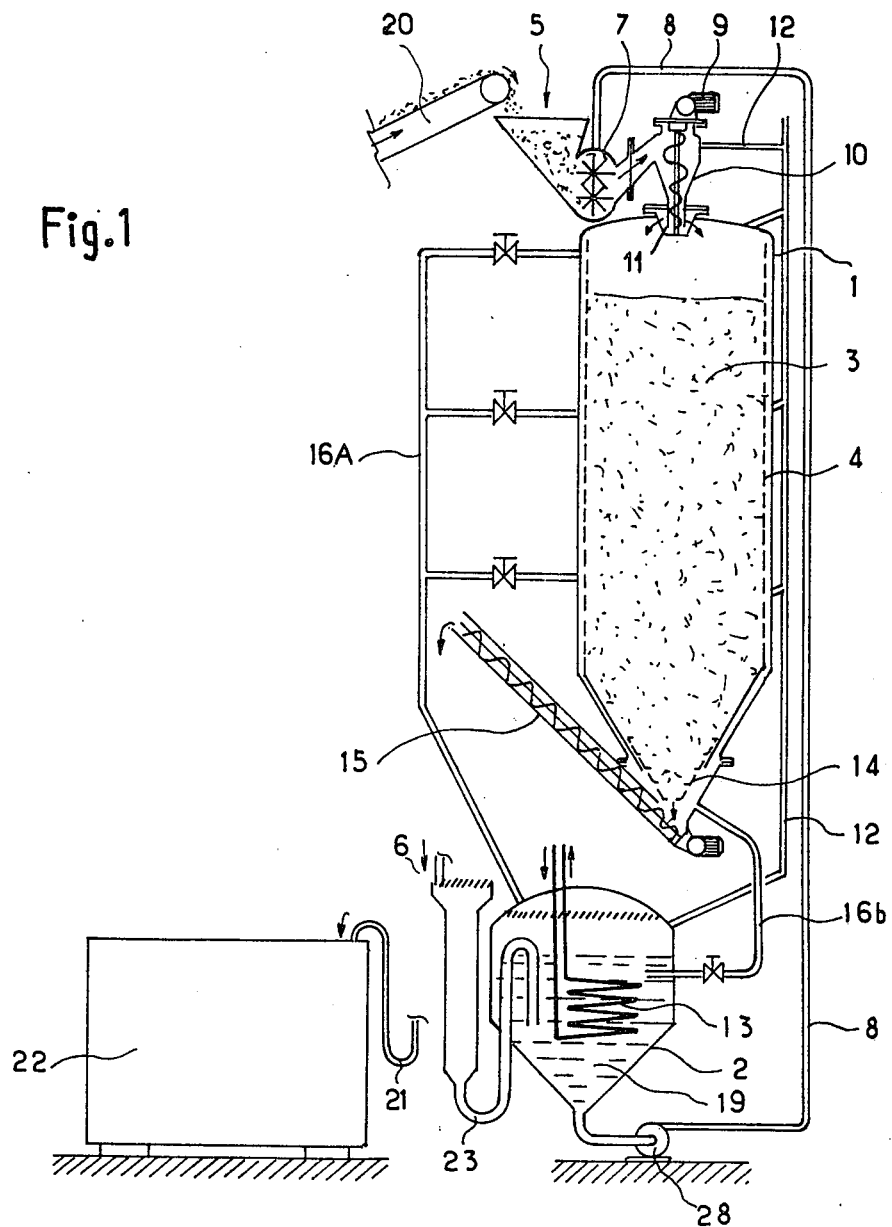
FIGS. 1 to 3 show diagrammatically an embodiment of an installation according to the present invention.

It must be well understood, however, that the installation described below and shown in the drawings, is given purely by way of illustration of an embodiment according to the invention, but does not constitute a limitation thereof in any way.

The installation according to the present invention which produces methane by anaerobic fermentation and is shown diagrammatically in FIG. 1 comprises, in nonlimiting manner, an upper cylindrical tank 1 at the top of which is located a distributing device 11 terminating the solid substrate feed device 5 (fed, for example, by conveyor belt 20). Feed device 5 is provided with a chopper 7. Thus solid substrate 3, before entering tank 1, is chopped into small pieces by chopper 7 and is sprinkled with liquor coming from liquid fermenter 2 arriving through the pipe 8. The mixture thus obtained is drawn by a movable organ equipped with a screw 24 driven by a motor 9, such as an Archimedes screw, pump or the like. Perforated basket 4 holds solid biomass 3, while the liquor flows by gravity through piping 16a, 16b, and the gas produced is collected through piping 12. After fermentation and the longer or shorter stay in tank 1, solid substrate 3, usable as fertilizer, is removed from vessel 1 by opening the manoeuverable grills by mechanical operation means located at the bottom of tank 1. The removal can take place, for example, by means of the hopper provided with discharge screw 15. Liquid substrate digestion tank 2 is located, for example, below tank 1 and by gravity receives the liquor coming from tank 1. It is fed directly by feed apparatus 6 with liquid substrate 19 and is provided with a coil 19 with circulating hot water, for example, for possible heating liquid substrate 19. The exhausted (and clear) liquor is sent by the pipe 21 (which can be connected to pipe 16b, at the bottom of the tank 1), into tank 22.

Figure 2:
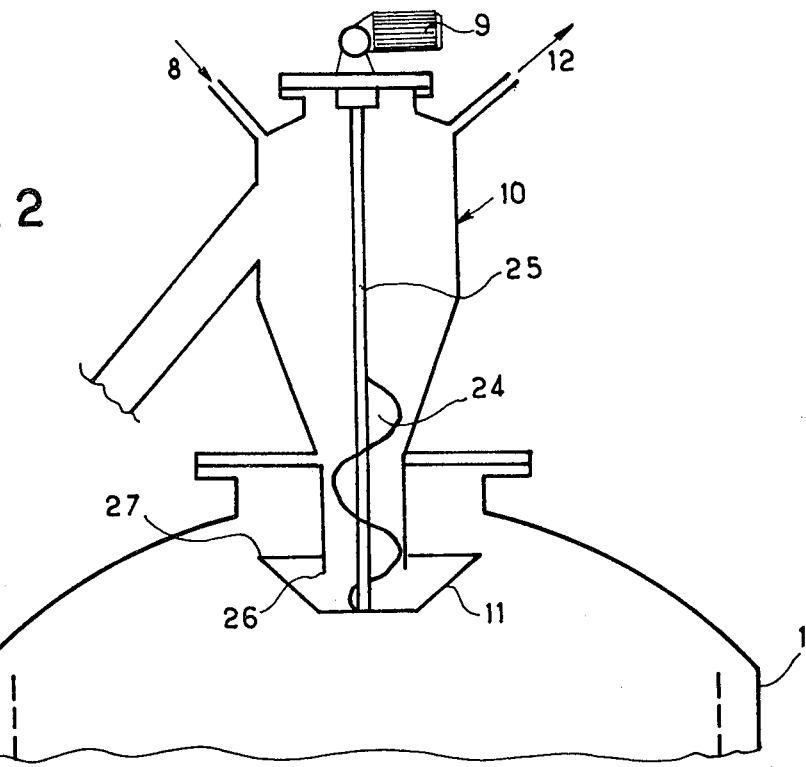

FIG. 2 shows in detail the driving organ for solid substrate feed device 5. The chopped substrate sprayed with liquor coming from tank 2 and arriving by pipe 8 (here placed after the chopper) is drawn into fermentation tank 1 by a feeder 10 the shaft 25 of which is provided at its lower part with a material-driving screw 24. This shaft rotates and is driven by motor 9. The unit constitutes a forced feed organ such as an Archimedes screw, pump or the like. It may also be provided at its lower part with a saucer 11 mounted so that its upper edge 27 is some centimeters higher than the bottom of feed pipe 26 which terminates the body of the feeder 10 of the feed device. This feed device is also connected through the pipe 12 to the methane storage tank.

Figure 3:
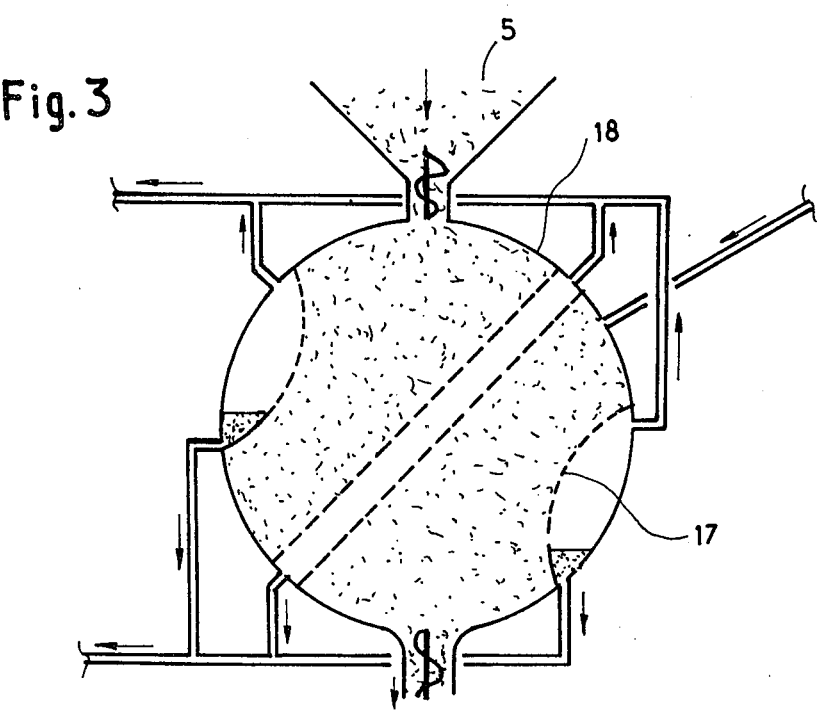

FIG. 3 shows another variant of a solid substrate fermentation tank; the tank has the shape of a spherical vessel 18 subdivided into several parts by perforated partitions 17.

The whole operation could, for example, proceed in the following manner: conveyor belt 20 brings the fresh manure and pours it into feed device 5. The manure is then chopped up by chopper 7 and liberally sprinkled with liquor coming from liquid substrate fermentation tank 2, which arrives through pipe 8. The liquor is brought to about 40° C. in contact with heating coil 18 which is located in tank 2. Chopper 7 and distributing saucer 11 are, each, provided with a water seal which constitutes the front and rear hydraulic seals of feed device 5. In this way, it is not possible to establish direct communication between the inside of tank 1 and the outer atmosphere; the considerable flow of hot liquor flowing through pipe 8, assists in the introduction of the fresh manure. The fresh manure, thus seeded and heated, is spread in the upper portion of the top part of tank 1 which acts as a percolator. Due to the presence of perforated basket 4, continuous draining of solid substrate and escape of the methane gas are performed. The outer jacket of tank 1 is preferably heat insulated. By pipes 16 (16a and 16b), the percolated liquor is directed to liquid substrate fermentation tank 2. Here it is mixed, for example, with fresh liquid manure introduced through the liquid substrate intake device 6, through a double siphon 23. Heating coil 13 keeps the temperature constant (about 40° C.). Hot liquor recycling pump 28 assures the return for seeding of the fresh material introduced into tank 1, and for heating of tank 1. By connecting to the pipe 16b, an overflow pipe (not shown in the drawing), which is connected to exhausted liquor removal pipe 21, and by stopping recycling of the hot liquor, tank 2 is completely filled and the exhausted liquor must follow pipe 21 and pour into exhausted liquor tank 22. This process ensures the automatic transfer from the overflow of the circulating liquor to exhausted liquor tank 22. At the bottom of tank 1, the exhausted manure is removed through a collection device which is constituted by grills equipped with a stripping mechanism 14 and with screw 15. Gas pipes 12 take off raw gas produced by the two tanks 1 and 2 to direct it for conditioning and use.

The operation of the installation as described, can be entirely automatic and needs only regulation of the temperature of the recycling liquor in tank 2 and of a suitable percolation flow rate.

It is evident from the foregoing description that, whatever the modes of operation, of embodiment and of application adopted, processes and installations are provided which have, with respect to processes and installations intended for the same purpose known previously, important advantages, of which some have been mentioned in the foregoing, particularly:

the advantage of being able to perform the fermentation continuously, automatically and with a minimum expenditure of energy;

the advantage of being able to optimize to the maximum the treatment of the composite substrates by the separation of the concentrated and solid substrates and of the dilute substrates;

the advantage of resulting in a solid residue homogeneous from the viewpoint of particle size, forming an easily transportable quality fertilizer and a clear and nonpolluting liquid effluent;

and the advantage of very great simplicity of operation, realizable "to order" as a function of the amount and the quality of the raw materials, on the operating site.

As is evident from the foregoing, the invention is in no way limited to those of its methods of practice, embodiments and applications which have been specifically described in the foregoing; it encompasses, on the contrary, all variants which may come to the mind of the technician skilled in the art, without departing from the context or scope of the present invention.

I claim:

1. Installation for the preparation of fuel gases by anaerobic fermentation, comprising a first tank (1) for the treatment of fermentable solids or concentrated liquids containing fermentable solids and having a solid content greater than 16%, said first tank being provided with a perforated partition means to permit drainage of liquid therethrough over almost the entire height of said first tank and allowing gases and liquids to circulate therethrough while holding solids from passing therethrough;

a second tank (2) for the treatment of dilute fermentatable liquids the dry content of which is less than 10%, said second tank having a heating coil (13) therein;

fermentable solids feeding means connected to the top of said first tank for feeding fermentable solids to said first tank, said fermentable solids feeding means comprising a chopper (7), a recirculation intake pipe (8) connected between said second tank and said feeding means for recycling liquor from said second tank to said fermentable solids feed device, and a conveyor means (25) for conveying a mixture of the recycling liquor from said intake pipe and fermentable solids from said chopper to said first tank;

means (6) for introducing fermentable liquid to said second tank;

means (14, 15) for collecting fermentation residue coming from said first tank;

connecting pipes (16a, 16b) extending between said first tank and said second tank for passing liquids from said first tank to said second tank from several different levels of said first tank; and a collector pipe (12) extending from the upper portion of said first tank and said second tank for collecting gases produced by fermentation.

2. An installation according to claim 1, wherein said conveyor means (25) comprises a driving screw (24) or a pump, said conveyor means further comprising a distributor element (11) downstream of said driving screw or pump.

3. An installation according to claim 1, wherein said perforated partition is in the form of a basket having a shape corresponding to the interior shape of said first tank.

4. An installation according to any one of claims 1, 2, or 3, wherein said first tank is located above said second tank so as to permit gravity flow of liquor coming from said first tank to said second tank.

* * * * *